United States Patent [19]

Thomas et al.

[11] 4,090,862
[45] May 23, 1978

[54] NOVEL PHENOXYCARBOXYLIC ACID ARYLOXY(THIO)CARBONYLAMINOMETHYL ESTERS AND THEIR USE FOR REGULATING PLANT GROWTH

[75] Inventors: Rudolf Thomas, Wuppertal; Klaus Lürssen, Bergisch-Gladbach, both of Germany

[73] Assignee: Bayer Aktiengesellschaft, Leverkusen, Germany

[21] Appl. No.: 753,407

[22] Filed: Dec. 22, 1976

[30] Foreign Application Priority Data

Jan. 15, 1976 Germany .............................. 2601376

[51] Int. Cl.² .................. A01N 9/12; A01N 9/24; C07C 69/76; C07C 153/07
[52] U.S. Cl. ......................................... 71/98; 71/100; 71/108; 71/109; 71/110; 260/455 A; 560/10; 560/17; 560/21; 560/23; 560/27; 560/28; 560/29; 560/56; 560/59; 560/61; 560/62
[58] Field of Search ............. 260/473 G; 71/108, 109, 71/110, 98; 560/23, 29, 61, 62

[56] References Cited

U.S. PATENT DOCUMENTS 2,818,424   12/1957   Zeile et al. ..................... 71/110 X Primary Examiner—Joseph Paul Brust
Attorney, Agent, or Firm—Burgess, Dinklage & Sprung

[57] ABSTRACT

Phenoxycarboxylic acid aryloxy(thio)carbonylaminomethyl ester compound of the formula

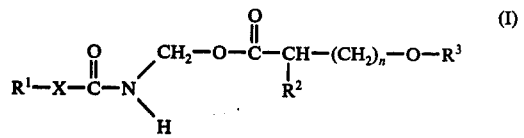

wherein
$R^1$ is phenyl, substituted phenyl, benzyl, substituted benzyl, naphthyl or substituted naphthyl,
$R^2$ is hydrogen or alkyl of from 1 to 4 carbon atoms,
$R^3$ is phenyl or substituted phenyl,
X is oxygen or sulfur, and
n is 0, 1 or 2 exhibit outstanding plant growth regulant properties.

22 Claims, No Drawings

NOVEL PHENOXYCARBOXYLIC ACID ARYLOXY(THIO)CARBONYLAMINOMETHYL ESTERS AND THEIR USE FOR REGULATING PLANT GROWTH

The present invention relates to certain new phenoxycarboxylic acid aryloxy(thio)carbonylaminomethyl compounds, to plant-growth regulating compositions containing them and to their use for regulating plant growth.

It is known that certain 2-halogenoethyltrialkylammonium halides exhibit plant-growth-regulating properties from U.S. Pat. No. 3,156,554. However, the action of this compound is not always entirely satisfactory, especially if low amounts and low concentrations are used.

Furthermore, it is known that a product that is commercially available under the name "Off-Shoot-T", and which is based on fatty alcohols with 6, 8, 10 and 12 carbon atoms, can be employed for regulating plant growth, in particular for suppressing the growth of side shoots of tobacco (see Farm Chemicals Handbook 1975, Meister Publishing Company, Willoughby, Ohio 1975, Pesticide Dictionary D147). However, the action of this compound is also not always entirely statisfactory, especially if low amounts and low concentrations are used.

The present invention provides, as new compounds, the phenoxycarboxylic acid aryloxy(thio)carbonylaminomethyl esters of the general formula

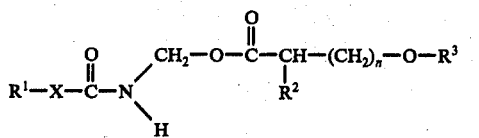

in which
R$^1$ is phenyl, substituted phenyl, benzyl, substituted benzyl, naphthyl or substituted naphthyl,
R$^2$ is hydrogen or alkyl of from 1 to 4 carbon atoms,
R$^3$ is phenyl or substituted phenyl,
X is oxygen or sulfur, and
$n$ is 0, 1 or 2

The compounds of the formula (I) have been found to exhibit powerful plant growth-regulating properties. Surprisingly, the phenoxycarboxylic acid aryloxy(thio)-carbonylaminomethyl esters of the formula (I) exhibit a better plant-growth-regulating action than the known preparations (2-chloroethyl)-trimethylammonium chloride and "Off-Shoot-T", these compounds being recognized to be highly active compounds of the same type of action. The active compounds according to the invention thus represent a valuable enrichment of the art.

Preferably, R$^1$ represents phenyl which optionally carries one or more substituents selected from halogen (especially fluorine, chlorine and bromine), alkyl with 1 to 4 carbon atoms, alkoxy with 1 to 4 carbon atoms, alkylthio with 1 to 4 carbon atoms, phenyl, phenoxy and trifluoromethyl, or represents benzyl, the phenyl ring of which optionally carries one or more substituents selected from halogen (especially fluorine, chlorine or bromine), alkyl with 1 to 4 carbon atoms, alkoxy with 1 to 4 carbon atoms, alkylthio with 1 to 4 carbon atoms, phenyl, phenoxy and trifluoromethyl, or represents naphthyl which optionally carries one or more substituents selected from halogen (especially fluorine, chlorine and bromine), alkyl with 1 to 4 carbon atoms, alkoxy with 1 to 4 carbon atoms, alkylthio with 1 to 4 carbon atoms, phenyl, phenoxy and trifluoromethyl; R$^2$ represents hydrogen or alkyl with 1 or 2 carbon atoms; and R$^3$ represents phenyl, which optionally carries one or more substituents selected from halogen (especially fluorine, chlorine and bromine), straight-chain or branched alkyl with 1 to 4 carbon atoms, alkoxy with 1 or 2 carbon atoms, halogenoalkyl with 1 to 2 carbon atoms and 1 to 5 halogen atoms (especially fluorine and chlorine), nitro and phenoxy which itself may be optionally substituted by fluorine, chlorine, bromine or nitro.

The present invention also provides a process for the preparation of a phenoxycarboxylic acid aryloxy(thio)-carbonylaminomethyl ester of the formula (I), in which an N-chloromethyl-carbamic acid ester of the general formula

in which
R$^1$ and X have the abovementioned meanings,
(a) is reacted with a phenoxycarboxylic acid of the general formula

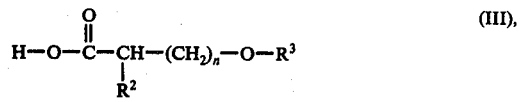

in which
R$^2$, R$^3$ and $n$ have the abovementioned meanings, in the presence of a diluent and in the presence of an acid-binding agent, or (b) is reacted with an alkali metal salt of a phenoxy carboxylic acid, of the general formula

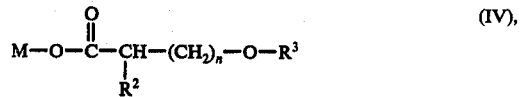

in which
R$^2$, R$^3$ and $n$ have the abovementioned meanings, and
M represents an alkali metal, preferably sodium or potassium, in the presence of a diluent.

If N-chloromethyl-carbamic acid 3-chlorophenyl ester and 2,4-dichlorophenoxyacetic acid are used as starting materials in process variant (a), the course of the reaction can be represented by the following equation:

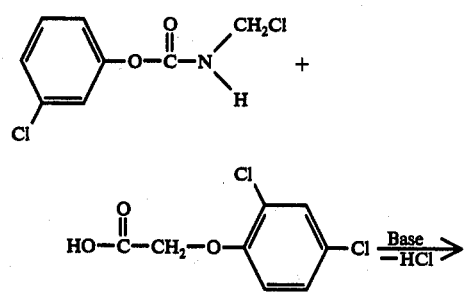

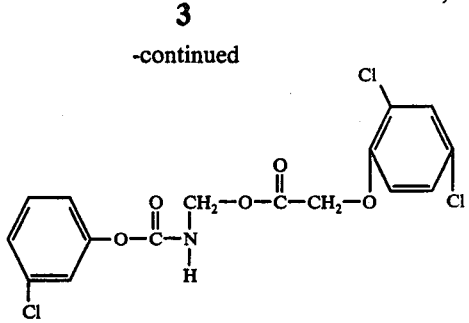

If N-chloromethyl-carbamic acid 2-chlorophenyl ester and the sodium salt of 2,4,5-trichlorophenoxyacetic acid are used as starting materials in process variant (b), the course of the reaction can be represented by the following equation:

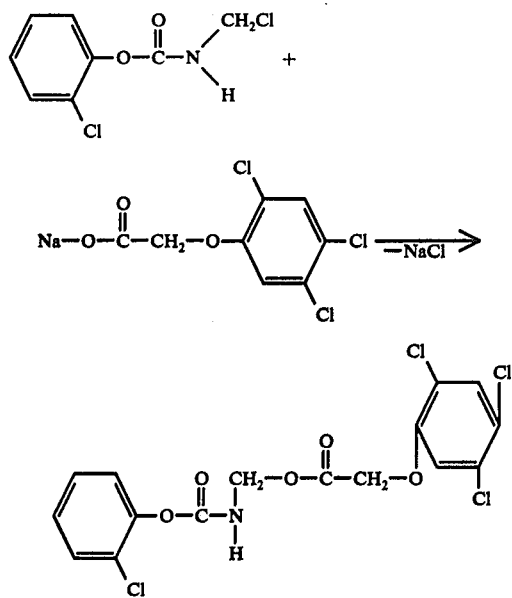

The N-chloromethyl-carbamic acid esters of the formula (II) which can be used according to the invention have hitherto only been described in part, in a general way, in the literature (see U.S. Pat. No. 3,376,335 and Belgian Specification No. 632,152). The compounds of the formula (II), including those that have not previously been described in the literature, can be prepared by reacting N-methoxymethyl-carbamic acid esters of the general formula

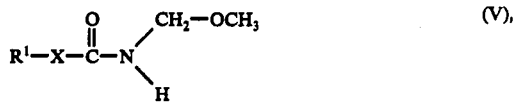

in which $R^1$ and X have the abovementioned meanings, with customary agents which split ethers, such as, for example, thionyl chloride, acetyl chloride, phosphorus oxychloride, or phosphorus pentachloride, in the presence of a diluent, such as, for example, carbon tetrachloride, at temperatures between 0° and 70° C. The reaction products are isolated by filtering off the precipitate formed during the reaction, and rinsing and drying it.

The N-methoxymethyl-carbamic acid esters of the formula (V) to be used as intermediates have hitherto also only been described in part, in a general way (see U.S. Pat. No. 3,376,335 and Belgian Patent Specification No. 632,152). The N-methoxymethyl-carbamic acid esters of the formula (V), including those which have not previously been described in the literature, can be prepared by reacting known compounds of the formula $$R^1 - X - H \qquad (VI),$$

in which $R^1$ and X have the abovementioned meanings, with methoxymethyl isocyanate in the presence of a diluent, such as, for example, carbon tetrachloride, and in the presence of a few drops of triethylamine as a catalyst, at temperatures between 0° and 80° C. The reaction products are isolated in a known manner. They are obtained, for example, by evaporating the reaction mixture after completion of the reaction, then taking up the residue in an organic solvent, washing this solution until it is neutral and then drying and evaporating it.

The following may be mentioned as examples of the N-chloromethyl-carbamic acid esters of the formula (II) which can be used according to the invention: N-chloromethyl-carbamic acid phenyl ester, 2-chlorophenyl ester, 4-bromophenyl ester, 4-fluorophenyl ester, 2,4-dichlorophenyl ester, 3-trifluoromethylphenyl ester, 3-methylphenyl ester, 4-methoxyphenyl ester, 4-methylthiophenyl ester, 4-biphenylyl ester, 4-phenoxyphenyl ester, phenylthio ester, 4-chlorophenylthio ester, benzyl ester, 4-chlorobenzyl ester, 3,4-dichlorobenzyl ester, 2,4-dichlorobenzyl ester, 2,4,6-trimethylbenzyl ester, 2,4-dibromobenzyl ester, naphthyl ester, 4-chloro-1-naphthyl ester and 4-ethyl-1-naphthyl ester.

The phenoxycarboxylic acids of the formula (III) which can be used according to the invention, and their alkali metal salts of the formula (IV), are generally known, easily accessible compounds (see, inter alia, J. Amer. Chem. Soc. 63, 1768 (1941); Chem.Ber. 57, 204 (1924); J.f.prakt. Chemie 114, 297 (1926) and Houben-Weyl, Methoden der organischen Chemie (Methods of Organic Chemistry), Volume 6/2, page 533, G. Thieme Verlag Stuttgart 1963).

The following may be mentioned as examples of the compounds of the formulae (III) and (IV): phenoxyacetic acid, 2,4-dichlorophenoxyacetic acid, 2,4-dimethylphenoxyacetic acid, 2,4,5-trichlorophenoxyacetic acid, 3-bromophenoxyacetic acid, 3-trifluoromethylphenoxyacetic acid, 4-tert.-butylphenoxyacetic acid, 2-ethoxyphenoxyacetic acid, 2,4-dichloro-6-nitrophenoxyacetic acid, 4-phenylphenoxyacetic acid, 2-phenoxyphenoxyacetic acid, 4-(4'-chlorphenoxy)-phenoxyacetic acid, 2-(3'-nitrophenoxy)-phenoxyacetic acid, α-phenoxypropionic acid, α-2,4,5-trichlorophenoxypropionic acid, α-4-ethylphenoxypropionic acid, α-4-chloro-2-methylphenoxypropionic acid, α-2-isopropoxyphenoxypropionic acid, β-phenoxypropionic acid, β-4-bromophenoxypropionic acid, β-2-methylphenoxypropionic acid, β-4-chloro-3-methylphenoxypropionic acid, β-3,4-difluorophenoxypropionic acid, α-phenoxybutyric acid, α-4-chlorophenoxybutyric acid, α-2,4-dichlorophenoxybutyric acid, α-3,4-dimethylphenoxybutyric acid, γ-phenoxybutyric acid, γ-2,4,5-trichlorophenoxybutyric acid, γ-2-ethyl-4-bromophenoxybutyric acid and γ-4-phenoxyphenoxybutyric acid, as well as the sodium salts and potassium salts of the phenoxycarboxylic acids listed here.

Diluents which can be used for the reaction according to the invention, in accordance with process variant (a), are preferably aprotic organic solvents, especially esters, such as ethyl acetate; nitriles, such as acetonitrile; aliphatic and aromatic hydrocarbons, such as hexane, benzine, benzene, toluene and xylene; sulphoxides, such as dimethylsulphoxide; ketones, such as acetone; ethers, such as diethyl ether and tetrahydrofurane; and halogenated hydrocarbons, such as carbon tetrachloride, chloroform, methylene chloride and dichloroethane.

The reaction according to the invention, in accordance with process variant (a), is carried out in the presence of an acid-binding agent. Acid-binding agents which can be used for this purpose are all customary inorganic and organic acid acceptors, especially alkali metal carbonates, such as sodium carbonate, potassium carbonate and sodium bicarbonate, and lower tertiary alkylamines, cycloalkylamines or aralkylamines, such as triethylamine and dimethylbenzylamine, as well as pyridine and diazabicyclo-octane.

In the process according to the invention, according to variant (a), the reaction temperature can be varied within a fairly wide range. In general, the reaction is carried out at between −20° C and 50° C, preferably between −10° C and 20° C.

In carrying out the process according to the invention in accordance with variant (a), preferably 1 mole of phenoxycarboxylic acid of the formula (III) and 1 to 1.1 moles of acid-binding agent are employed per mole of N-chloromethylcarbamic acid ester of the formula (II).

To isolate the compounds of the formula (I), the chloride formed during the reaction is filtered off and the filtrate is washed neutral with water, dried over sodium sulphate and freed from the solvent under reduced pressure. The residue is purified by recrystallization, if required.

For the reaction according to the invention, in accordance with process variant (b), diluents which can be used are preferably aprotic organic solvents, especially the solvents already mentioned in connection with variant (a).

In process variant (b) the reaction temperatures can be varied within a fairly wide range. In general, the reaction is carried out at between 0° C and 80° C, preferably between 0° C and 60° C.

In carrying out the process according to the invention, in accordance with variant (b), preferably 1 mole of an alkali metal salt of a phenoxycarboxylic acid, of the formula (IV), is employed per mole of N-chloromethylcarbamic acid ester of the formula (II).

To isolate the compounds according to the invention, of the formula (I), the reaction solution is filtered and the filtrate is concentrated by distilling off the solvent. The residue is purified by recrystallization, if required.

The following may be mentioned as individual examples of the phenoxycarboxylic acid aryloxy(thio)carbonylaminoethyl esters according to the invention: 2-phenoxyacetic acid phenoxycarbonylaminomethyl ester, 2-phenoxyacetic acid 2-chlorophenoxycarbonylaminomethyl ester, 2-phenoxyacetic acid 4-bromophenoxycarbonylaminomethyl ester, 2-phenoxyacetic acid 4-fluorophenoxycarbonylaminomethyl ester, 2-phenoxyacetic acid 2,4-dichlorophenoxycarbonylaminomethyl ester, 2-phenoxyacetic acid 3-trifluoromethylphenoxycarbonylaminomethyl ester, 2-phenoxyacetic acid 3-methylphenoxycarbonylaminomethyl ester, 2-phenoxyacetic acid 4-methoxyphenoxycarbonylaminomethyl ester, 2-phenoxyacetic acid 4-methylthiophenoxycarbonylaminomethyl ester, 2-phenoxyacetic acid 4-phenylphenoxycarbonylmethylaminomethyl ester, 2-phenoxyacetic acid 4-phenoxyphenoxycarbonylaminomethyl ester, 2-phenoxyacetic acid phenylthiocarbonylaminomethyl ester, 2-phenoxyacetic acid benzyloxycarbonylaminomethyl ester, 2-phenoxyacetic acid 4-chlorophenylthiocarbonylaminomethyl ester, 2-phenoxyacetic acid 4-chlorobenzyloxycarbonylaminomethyl ester, 2-phenoxyacetic acid 3,4-dichlorobenzyloxycarbonylaminomethyl ester, 2-phenoxyacetic acid 2,4-dichlorobenzyloxycarbonylaminomethyl ester, 2-phenoxyacetic acid, 2,4,6-trimethylbenzyloxycarbonylaminomethyl ester, 2-phenoxyacetic acid 2,4-dibromobenzyloxycarbonylaminomethyl ester, 2-phenoxyacetic acid naphth-1-oxycarbonylaminomethyl ester, 2-phenoxyacetic acid 4-chloronaphth-1-oxycarbonylaminomethyl ester, 2-phenoxyacetic acid 4-ethylnaphth-1-oxycarbonylaminomethyl ester, 2-(2,4-dichlorophenoxy)-acetic acid phenoxycarbonylaminomethyl ester, 2-(2,4-dimethylphenoxy)-acetic acid phenoxycarbonylaminomethyl ester, 2-(2,4,5-trichlorophenoxy)-acetic acid phenoxycarbonylaminomethyl ester, 2-(3-bromophenoxy)-acetic acid phenoxycarbonylaminomethyl ester, 2-(3-trifluoromethylphenoxy)-acetic acid phenoxycarbonylaminomethyl ester, 2-(4-tert.-butylphenoxy)-acetic acid phenoxycarbonylaminomethyl ester, 2-(2-ethoxyphenoxy)-acetic acid phenoxycarbonylaminomethyl ester, 2-(2,4-dichloro-6-nitrophenoxy)-acetic acid phenoxycarbonylaminomethyl ester, 2-(4-phenylphenoxy)-acetic acid phenoxycarbonylaminomethyl ester, 2-(2-phenoxyphenoxy)-acetic acid phenoxycarbonylaminomethyl ester, 2-[4-(4'-chlorophenoxy)-phenoxy]-acetic acid phenoxycarbonylaminomethyl ester, 2-[2-(3'-nitrophenoxy)-phenoxy]-acetic acid phenoxycarbonylaminomethyl ester, α-(phenoxy)-propionic acid phenoxycarbonylaminomethyl ester, α-(2,4,5-trichlorophenoxy)-propionic acid phenoxycarbonylaminoethyl ester, α-(4-ethylphenoxy)-propionic acid phenoxycarbonylaminomethyl ester, α-(4-chloro-2-methylphenoxy)-propionic acid phenoxycarbonylaminomethyl ester, α-(2-isopropoxyphenoxy)-propionic acid phenoxycarbonylaminomethyl ester, β-(phenoxy)-propionic acid phenoxycarbonylaminomethyl ester, β-(4-bromophenoxy)-propionic acid phenoxycarbonylaminomethyl ester, β-(2-methylphenoxy)-propionic acid phenoxycarbonylaminomethyl ester, β-(4-chloro-3-methylphenoxy)-propionic acid phenoxycarbonylaminomethyl ester, β-(3,4-difluorophenoxy)-propionic acid phenoxycarbonylaminomethyl ester, α-(phenoxy)-butyric acid phenoxycarbonylaminomethyl ester, α-(4-chlorophenoxy)-butyric acid phenoxycarbonylaminomethyl ester, α-(2,4-dichlorophenoxy)-butyric acid phenoxycarbonylaminomethyl ester, α-(3,4-dimethylphenoxy)-butyric acid phenoxycarbonylaminomethyl ester, γ-(phenoxy)-butyric acid phenoxycarbonylaminomethyl ester, γ-(2,4,5-trichlorophenoxy)-butyric acid phenoxycarbonylaminomethyl ester, γ-(2-ethyl-4-bromophenoxy)-butyric acid phenoxycarbonylaminomethyl ester and γ-(4-phenoxyphenoxy)-butyric acid phenoxycarbonylaminomethyl ester.

The active compounds according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland lines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which again counteracts lodging.

In the case of many crop plants, inhibition of the vegetative growth permits denser planting of the crop, so that a greater yield per area of ground can be achieved. A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit — for example in the case of table fruit — in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out completely mechanical or manual havesting in only a single pass, for example in the case of tobacco, tomatoes or coffee.

By using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds, such as fungicides, insecticides, acaricides and herbicides, and also as a mixture with fertilisers.

The formulations in general contain from 0.1 to 95 percent by weight of active compound, preferably from 0.5 to 90 percent by weight.

The active compounds can be used as such, in the form of their formulations or as the use forms prepared therefrom such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming, gassing and the like. Furthermore it is possible to apply the active compounds in accordance with the ultra-low-volume (ULV) method, to spread the active-compound preparation or the active compound itself on plants or parts of plants or to inject the active-compound preparation or the active compound itself into the soil. It is also possible to treat the seeds of the plant.

The amount of active compound employed can be varied within a fairly wide range. In general, between 0.01 and 50 kg, preferably between 0.05 and 10 kg, of active compound are employed per hectare of soil surface.

The preferred period of time within which the growth regulators are applied depends on the climatic and vegetative circumstances.

The compounds according to the invention not only have plant-growth-regulating properties but also possess a herbicidal activity.

The present invention also provides a plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides means of yielding plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Examples, in which each compound of the present invention is identified by the number of the corresponding preparative Example.

EXAMPLE A

Inhibition of growth/beans
Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration with water.

Young bean plants, in the stage in which the primary leaves had unfolded completely, were sprayed with the preparations of active compound until dripping wet. After 2 weeks, the additional growth was measured and the inhibition of growth in % of the additional growth of the control plants was calculated. 100% means that growth had stopped and 0% denotes a growth corresponding to that of the untreated control plants.

The active compounds, the active-compound concentrations and results can be seen from the table which follows:

Table A

| Active compound | Inhibition of growth/beans | |
| --- | --- | --- |
| | Active compound concentration in % | Inhibition of growth in % |
| — (control) | — | 0 |
| (3) | 0.05 | 100 |
| (29) | 0.05 | 80 |

EXAMPLE B

Inhibition of growth/chrysanthemums
Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration with water.

Chrysanthemum cuttings of about 10 cm height were sprayed with the preparations of active compound until dripping wet. As soon as the untreated control plants had grown to a height of about 40 cm, the additional growth of all plants was measured and the inhibition of growth was calculated in % of the additional growth of the control plants. 100% meant that growth had stopped and 0% denoted a growth corresponding to that of the untreated control plants.

The active compounds, active-compound concentrations and results can be seen from the table which follows:

Table B

| Active compound | Inhibition of growth/chrysanthemums | |
| --- | --- | --- |
| | Active compound concentration in % | Inhibition of of growth in % |
| — (control) | — | 0 |

Table B-continued

| Inhibition of growth/chrysanthemums | | |
|---|---|---|
| Active compound | Active compound concentration in % | Inhibition of growth in % |
| (29) | 0.1 | 90 |

EXAMPLE C

Inhibition of the growth of side shoots of tobacco
Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration with water.

The shoot tips of about 50 cm high tobacco plants were broken off. On the following day, the plants were sprayed with the preparations of active compound until dripping wet. After 3 weeks, the side shoots which had formed during this time were broken off and weighed. The weight of the side shoots of the treated plants was compared with the weight of the side shoots of the untreated control plants and expressed in %. 100% inhibition denoted the absence of side shoots and 0% denoted a growth of side shoots which corresponded to that of the control plants.

The active compounds, active-compound concentrations and results can be seen from the table which follows:

Table C

| Inhibition of the growth of side shoots of tobacco | | |
|---|---|---|
| Active compound | Active compound concentration in % | Inhibition of the growth of side shoots in % |
| — (control) | — | 0 |
| Off-Shoot-T* | 0.2 | 20 |
| (28) | 0.2 | 97 |
| (29) | 0.2 | 98 |
|  | 0.05 | 92 |

*Off-Shoot-T: a commercially available growth regulator based on fatty alcohols with 6, 8, 10 and 12 carbon atoms.

EXAMPLE D

Influence on growth/wheat
Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration with water.

Young wheat plants in the 2-leaf stage were sprayed with the preparation of active compound until dripping wet. After 3 weeks, the additional growth was measured and the influence on growth was calculated in % of the additional growth of the control plants. 0% denoted a growth which corresponded to that of the control plants. Positive values characterized a promotion of growth in comparison to the control plants while negative values correspondingly indicated an inhibition of growth.

The active compounds, active-compound concentrations and results can be seen from the table which follows:

Table D

| Influence on growth/wheat | | |
|---|---|---|
| Active compound | Active compound concentration in % | Influence on growth in % |
| — (control) | — | 0 |
| (29) | 0.05 | −45 |
| (28) | 0.05 | −50 |
| (18) | 0.05 | −60 |
| ( 2) | 0.05 | −50 |
| ( 4) | 0.05 | +35 |
| ( 7) | 0.05 | −45 |
| (35) | 0.05 | −29 |
| (45) | 0.05 | −45 |
| (51) | 0.05 | −45 |
| (55) | 0.05 | −65 |
| (49) | 0.05 | −55 |

EXAMPLE E

Influence of growth of trees (*Alnus glutinosa*)
Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration with water.

One-year-old seedlings which had grown to a height of about 25 cm were sprayed with the preparation of active compound until dripping wet. After 6 weeks' growth in a greenhouse, the additional growth was measured and the influence on growth was calculated in % of the additional growth of the control plants. 0% denoted a growth which corresponded to that of the control plants. Positive values characterized a promotion in growth in comparison to the control plants while negative values correspondingly indicated an inhibition of growth.

The active compounds, active compound concentrations and results can be seen from the table which follows:

Table E

| Influence on growth of woody plants (*Alnus glutinosa*) | | |
|---|---|---|
| Active compound | Active compound concentration in % | Influence on growth in % |
| — (control) | — | 0 |
| (24) | 0.2 | +11 |
|  | 0.1 | +93 |

EXAMPLE F

Influence of growth of trees (*Acer pseudoplatanus*)
Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration with water.

One-year-old seedlings which had grown to a height of about 25 cm were sprayed with the preparation of active compound until dripping wet. After 6 weeks' growth in a greenhouse, the additional growth was measured and the influence on growth was calculated in % of the additional growth of the control plants. 0% denoted a growth which corresponded to that of the control plants. Positive values characterized a promotion in growth in comparison to the control plants while negative values correspondingly indicated an inhibition of growth.

The active compounds, active-compound concentrations and results can be seen from the table which follows:

Table F

| | Influence on growth of woody plants *Acer pseudoplatanus* | |
|---|---|---|
| Active compound | Active compound concentration in % | Influence on growth in % |
| — (control) | — | 0 |
| ( 3) | 0.1 | −75 |
| (24) | 0.2 | −14 |
| | 0.1 | +34 |

EXAMPLE G

Inhibition of growth of grass (*Festuca pratensis*)
Solvent: 10 parts by weight of methanol
Emulsifier: 2 parts by weight of polyethylene-sorbitan monolaurate To prepare a suitable preparation of active compound, 1 part by weight of active compound was mixed with the stated amount of solvent and emulsifier and the mixture was made up to the desired concentration with water.

Grass was grown in plastic pots of size 7 cm × 7 cm and when it had grown to a height of about 5 cm was sprayed with the preparations of active compound until dripping wet. After 3 weeks, the additional growth was measured and the inhibition of growth in % of the additional growth of the untreated control plants was calculated. 100% meant that growth had stopped and 0% denoted a growth corresponding to that of the control plants.

The active compounds, active-compound concentrations and results can be seen from the table which follows:

Table G

| | Inhibition of growth of grass (*Festuca pratensis*) | |
|---|---|---|
| Active compound | Active compound concentration in % | Inhibition of growth in % |
| — (control) | — | 0 |
| $ClCH_2CH_2N^{\oplus}(CH_3)_3Cl^{\ominus}$ (known) | 0.05 | 0 |
| (24) | 0.05 | 50 |
| (51) | 0.05 | 55 |
| (54) | 0.05 | 90 |
| (5) | 0.05 | 50 |

EXAMPLE H

Inhibition of growth/soya beans
Solvent: 10 parts by weight of methanol
Emulsifier: 2 parts by weight of polyethylene-sorbitan monolaurate To prepare a suitable preparation of active compound, 1 part by weight of active compound was mixed with the stated amount of solvent and emulsifier and the mixture was made up to the desired concentration with water.

Young soya bean plants, in the stage in which the first secondary leaves had unfolded, were sprayed with the preparation of active compound until dripping wet. After 2 weeks, the additional growth was measured and the inhibition of growth in % of the additional growth of the control plants was calculated. 100% meant that growth had stopped and 0% denoted a growth corresponding to that of the untreated control plants.

The active compounds, active-compound concentrations and results can be seen from the table which follows:

Table H

| | Inhibition of growth/soya beans | |
|---|---|---|
| Active compounds | Active compound concentration in % | Inhibition of growth in % |
| — (control) | — | 0 |
| $ClCH_2CH_2N^{\oplus}(CH_3)_3Cl^{\ominus}$ (known) | 0.05 | 0 |
| (24) | 0.05 | 70 |
| (12) | 0.05 | 70 |
| (42) | 0.05 | 85 |
| (10) | 0.05 | 35 |

EXAMPLE I

Inhibition of growth/barley
Solvent: 10 parts by weight of methanol
Emulsifier: 2 parts by weight of polyethylene-sorbitan monolaurate To prepare a suitable preparation of active compound, 1 part by weight of active compound was mixed with the stated amount of solvent and emulsifier and the mixture was made up to the desired concentration with water.

Young barley plants, in the 2-leaved stage, were sprayed with the preparation of active compound until dripping wet. After the untreated control plants had reached a growth height of about 60 cm, the additional growth of all plants was measured and the inhibition of growth in % of the additional growth of the control plants was calculated. 100% meant that growth stopped and 0% denoted a growth corresponding to that of the control plants.

The active compounds, active compound concentrations and results can be seen from the table which follows:

Table I

| | Inhibition of growth/barley | |
|---|---|---|
| Active compound | Active compound concentration in % | Inhibition of growth in % |
| — (control) | — | 0 |
| $ClCH_2CH_2N^{\oplus}(CH_3)_3Cl^{\ominus}$ (known) | 0.05 | 20 |
| (29) | 0.05 | 65 |
| (28) | 0.05 | 35 |
| (18) | 0.05 | 65 |
| ( 2) | 0.05 | 75 |
| (20) | 0.05 | 30 |
| ( 7) | 0.05 | 75 |
| (25) | 0.05 | 40 |
| (16) | 0105 | 40 |
| (35) | 0.05 | 35 |
| ( 8) | 0.05 | 35 |
| (37) | 0.05 | 35 |
| (45) | 0.05 | 85 |
| (51) | 0.05 | 35 |
| (55) | 0.05 | 80 |
| (49) | 0.05 | 60 |

Table I-continued

| Active compound | Inhibition of growth/barley | |
|---|---|---|
| | Active compound concentration in % | Inhibition of growth in % |
| (11) | 0.05 | 40 |

The process of the present invention is illustrated by the following preparative Examples.

EXAMPLE 1 (process variant (a))

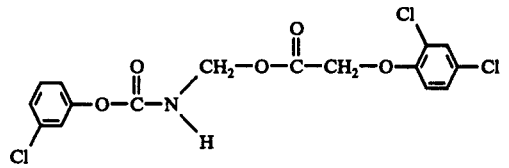 (1)

A solution of 220.1 g (1 mole) of N-chloromethylcarbamic acid 3-chlorophenyl ester in 1 liter of anhydrous ethyl acetate was added dropwise at 0° to 10° C to a mixture of 221 g (1 mole) of 2,4-dichlorophenoxyacetic acid and 111.3 g (1.1 moles) of triethylamine in 2 liters of ethyl acetate. The mixture was stirred for a further 15 hours at 20° C and was cooled to 5° C, and the triethylammonium chloride which had precipitated was filtered off. The filtrate was washed neutral with water and was concentrated in vacuo by distilling off the solvent. The solid residue was recrystallised from ether. 290 g (71.8% of theory) of 2-(2,4-dichlorophenoxy)-acetic acid 3-chlorophenoxycarbonylaminomethyl ester were obtained in the form of white crystals of melting point 110° C.

EXAMPLE 2 (process variant (b))

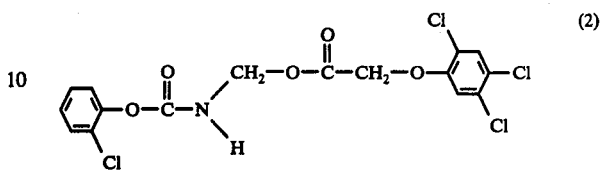 (2)

A solution of 220 g (1 mole) of N-chloromethylcarbamic acid 2-chlorophenyl ester in 1 liter of anhydrous acetonitrile was added dropwise to a suspension of 277.5 g (1 mole) of sodium 2,4,5-trichlorophenoxyacetate in 2 liters of anhydrous acetonitrile. After the exothermic reaction had subsided, the mixture was stirred for a further 15 hours at room temperature. It was then filtered and the filtrate was concentrated in vacuo by distilling off the solvent. The residue was recrystallised from ether/benzine. 354 g (80.6% of theory) of 2-(2,4,5-trichlorophenoxy)-acetic acid 2-chlorophenoxycarbonylaminomethyl ester were obtained in the form of white crystals of melting point 119° C.

The compounds listed in Table 1 which follows were obtained by procedures analogous to those of Examples 1 and 2.

Table 1

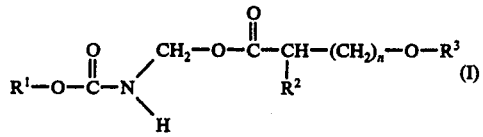 (I)

| Example No. | R$^1$ | R$^2$ | R$^3$ | n | Melting point (° C) or refractive index ($n_{20}^D$) |
|---|---|---|---|---|---|
| 3 | Cl, Cl-phenyl-CH$_2$- | H | Cl-phenyl-Cl | 0 | 63 |
| 4 | C(CH$_3$)$_3$, CH$_3$, C(CH$_3$)$_3$-phenyl | CH$_3$ | Cl-phenyl-Cl | 0 | 115 |
| 5 | C(CH$_3$)$_3$, CH$_3$, C(CH$_3$)$_3$-phenyl | H | Cl-phenyl | 0 | 119 |
| 6 | C(CH$_3$)$_3$, CH$_3$, C(CH$_3$)$_3$-phenyl | H | Cl-phenyl-Cl | 0 | 125 |

Table 1-continued
$$R^1-O-\overset{O}{\underset{}{C}}-\underset{H}{\overset{}{N}}-CH_2-O-\overset{O}{\underset{}{C}}-\underset{R^2}{\overset{}{CH}}-(CH_2)_n-O-R^3 \quad (I)$$
| Example No. | R¹ | R² | R³ | n | Melting point (° C) or refractive index ($n_{20}^D$) |
|---|---|---|---|---|---|
| 7 | 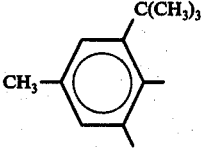 | H | 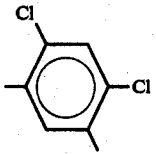 | 0 | 162 |
| 8 | 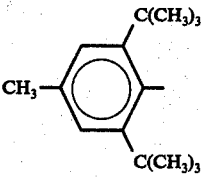 | CH₃ | 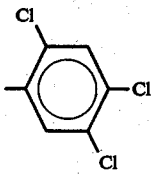 | 0 | 152 |
| 9 |  | CH₃ | 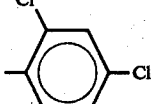 | 0 | 152 |
| 10 |  | H | 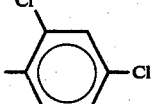 | 0 | 105 |
| 11 | 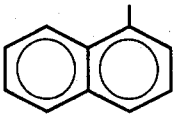 | H | 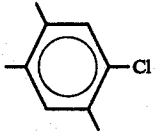 | 0 | 133 |
| 12 | 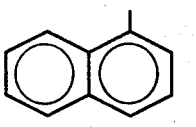 | CH₃ | 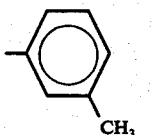 | 0 | 105 |
| 13 | 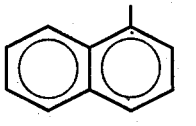 | CH₃ | 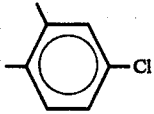 | 0 | 115 |
| 14 | 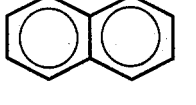 | H | 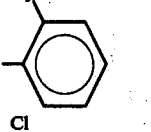 | 1 | 1.5691 |
| 15 | 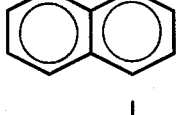 | H | 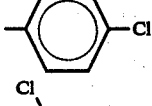 | 0 | 136 |
| 16 | 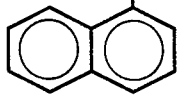 | CH₃ | 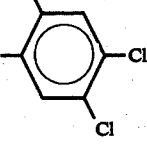 | 0 | 112 |

Table 1-continued $$R^1-O-\overset{O}{\overset{\|}{C}}-\underset{H}{N}-CH_2-O-\overset{O}{\overset{\|}{C}}-\underset{R^2}{CH}-(CH_2)_n-O-R^3 \quad (I)$$

| Example No. | R¹ | R² | R³ | n | Melting point (° C) or refractive index ($n_{20}^D$) |
|---|---|---|---|---|---|
| 17 | 2-Cl-C₆H₄ | CH₃ | 2,4-Cl₂-C₆H₃ | 0 | 106 |
| 18 | 2-Cl-C₆H₄ | H | 2,4-Cl₂-C₆H₃ | 0 | 119 |
| 19 | 2-Cl-C₆H₄ | H | 2-Cl-C₆H₄ | 0 | 1.5573 |
| 20 | 2-Cl-C₆H₄ | CH₃ | 4-(4-Cl-C₆H₄-O)-C₆H₄ | 0 | 118 |
| 21 | 2-Cl-C₆H₄ | H | 2-CH₃-4-Cl-C₆H₃ | 0 | 92 |
| 22 | 2-Cl-C₆H₄ | H | 2-CH₃-C₆H₄ | 1 | 1.5449 |
| 23 | 2-Cl-C₆H₄ | H | 2,4-Cl₂-C₆H₃ | 2 | 1.5490 |
| 24 | 2-Cl-C₆H₄ | CH₃ | 3-CH₃-C₆H₄ | 0 | 86 |
| 25 | 2-Cl-C₆H₄ | CH₃ | 2,4,5-Cl₃-C₆H₂ | 0 | 115 |
| 26 | 3-Cl-C₆H₄ | H | C₆H₅ | 0 | viscous oil |
| 27 | 3-Cl-C₆H₄ | H | 2-Cl-C₆H₄ | 0 | 123 |

Table 1-continued $$R^1-O-\overset{O}{\underset{H}{C}}-N-CH_2-O-\overset{O}{C}-\underset{R^2}{CH}-(CH_2)_n-O-R^3 \quad (I)$$

| Example No. | $R^1$ | $R^2$ | $R^3$ | n | Melting point (° C) or refractive index ($n_{20}^D$) |
|---|---|---|---|---|---|
| 28 | 3-Cl-phenyl | H | 3,4-Cl$_2$-phenyl | 0 | 108 |
| 29 | 2,4-Cl$_2$-phenyl | H | 2,4-Cl$_2$-phenyl | 0 | 93 |
| 30 | 2,4-Cl$_2$-phenyl | CH$_3$ | 2,4-Cl$_2$-phenyl | 0 | 126 |
| 31 | 2,4-Cl$_2$-phenyl | H | 2-Cl-phenyl | 0 | 1.5771 |
| 32 | 2,4-Cl$_2$-phenyl | H | 2,4-Cl$_2$-phenyl | 2 | 1.5538 |
| 33 | 2,4-Cl$_2$-phenyl | H | 3,4-Cl$_2$-phenyl | 0 | 123 |
| 34 | 2,4-Cl$_2$-phenyl | H | 2-CH$_3$-phenyl | 1 | 92 |
| 35 | 2,4-Cl$_2$-phenyl | CH$_3$ | 3,4-Cl$_2$-phenyl | 0 | 145 |
| 36 | 2,3-Cl$_2$-phenyl | H | 2,4-Cl$_2$-phenyl | 0 | 143 |
| 37 | 2,3-Cl$_2$-phenyl | H | 3,4-Cl$_2$-phenyl | 0 | 153 |

Table 1-continued
$$R^1-O-\overset{O}{\underset{H}{C}}-N-CH_2-O-\overset{O}{\underset{R^2}{C}}-CH-(CH_2)_n-O-R^3 \quad (I)$$
| Example No. | R¹ | R² | R³ | n | Melting point (° C) or refractive index ($n_{20}^D$) |
|---|---|---|---|---|---|
| 38 | 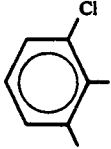 | H | 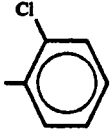 | 0 | 102 |
| 39 | 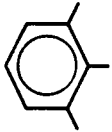 | CH₃ | 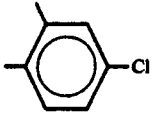 | 0 | 123 |
| 40 | 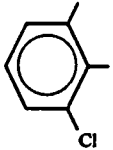 | H | 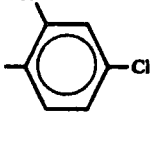 | 0 | 121 |
| 41 | 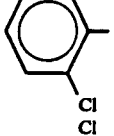 | H | 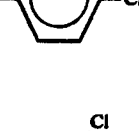 | 0 | 110 |
| 42 | 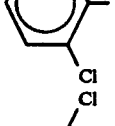 | H | 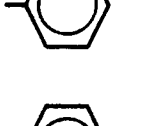 | 0 | 95 |
| 43 | 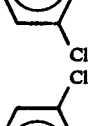 | H | 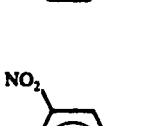 | 0 | 126 |
| 44 | 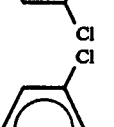 | H | 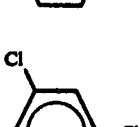 | 0 | 129 |
| 45 | 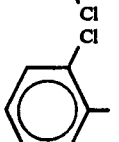 | CH₃ | 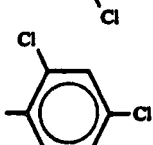 | 0 | 143 |
| 46 |  | H |  | 2 | 99 |

Table 1-continued
$$R^1-O-\overset{O}{\underset{\|}{C}}-\underset{\underset{H}{|}}{N}-CH_2-O-\overset{O}{\underset{\|}{C}}-\underset{\underset{R^2}{|}}{CH}-(CH_2)_n-O-R^3 \quad (I)$$
| Example No. | R¹ | R² | R³ | n | Melting point (°C) or refractive index ($n_{20}^D$) |
|---|---|---|---|---|---|
| 47 | 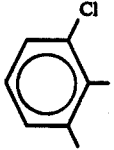 | H | 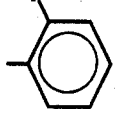 | 1 | 88 |
| 48 | 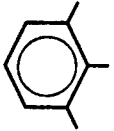 | CH₃ |  | 0 | 97 |
| 49 | 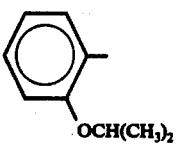 | CH₃ | 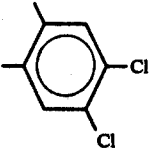 | 0 | viscous oil |
| 50 | 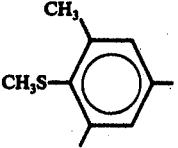 | H | 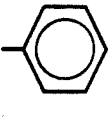 | 0 | 105 |
| 51 | 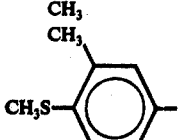 | H | 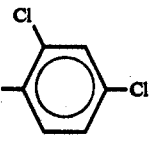 | 0 | 122 |
| 52 | 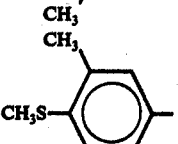 | H | 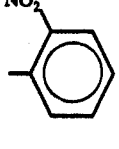 | 0 | 103 |
| 53 | 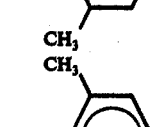 | H | 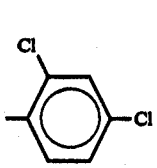 | 2 | 82 |
| 54 | 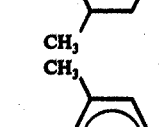 | H | 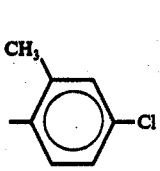 | 2 | 124 |
| 55 | 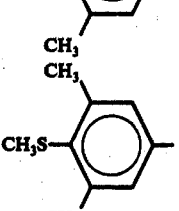 | CH₃ | 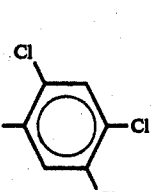 | 0 | 135 |

Table 1-continued $$R^1-O-\overset{O}{\underset{}{C}}-N\underset{H}{\overset{CH_2-O-\overset{O}{\underset{}{C}}-CH-(CH_2)_n-O-R^3}{\diagup}} \quad (I)$$
$$\phantom{R^1-O-C-N}\phantom{CH_2-O-C-}\phantom{CH-}R^2$$

| Example No. | R¹ | R² | R³ | n | Melting point (°C) or refractive index ($n_{20}^D$) |
|---|---|---|---|---|---|
| 56 | 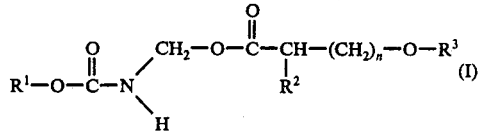 | H | 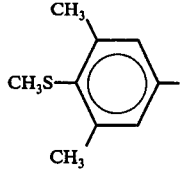 | 1 | 1.5530 |

PREPARATION OF THE STARTING MATERIALS

Example Ia

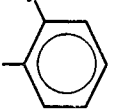

62 ml (0.85 mole) of thionyl chloride were added to 167 g (0.775 mole) of N-methoxymethylcarbamic acid 3-chlorophenyl ester in 200 ml of carbon tetrachloride. After the evolution of gas had ceased, the mixture was cooled to 0° C, while keeping the reaction mixture stirrable by adding carbon tetrachloride. The precipitate which had separated out was filtered off, rinsed with cold carbon tetrachloride and dried in vacuo at 40° C. 119.5 g (70% of theory) of N-chloromethylcarbamic acid 3-chlorophenyl ester of melting point 90° C were obtained.

The compounds listed in Table 2 which follows were prepared analogously:

Table 2

$$R^1-X-\overset{O}{\underset{}{C}}-N\underset{H}{\overset{CH_2Cl}{\diagup}} \quad (II)$$

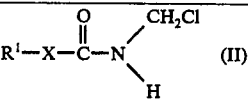

| Example No. | R¹ | X | Melting point (°C) |
|---|---|---|---|
| IIa | 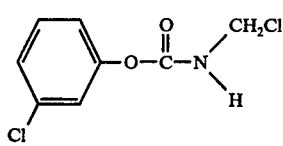 | O | 106 |
| IIIa | 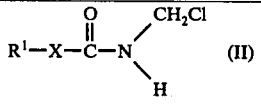 | O | 83 |
| IVa | 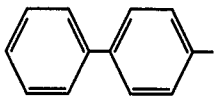 | O | 203 |
| Va | 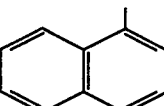 | O | 77 |
| VIa | 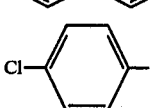 | O | 102 |
| VIIa | 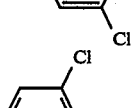 | O | 116 |
| VIIIa | 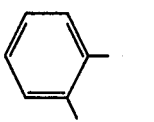 | O | 127 |
| IXa | 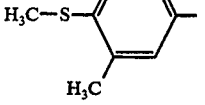 | O | 112 |
| Xa | 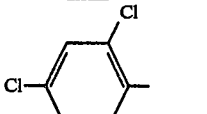 | O | 110 |
| XIa | | O | 96 |
| XIIa | | O | 120 |

Table 2-continued $$R^1-X-\overset{\overset{O}{\|}}{C}-\underset{H}{N}-CH_2Cl \quad (II)$$

| Example No. | R¹ | X | Melting point (° C) |
|---|---|---|---|
| XIIIa | 4-CH₃O-C₆H₄- | O | 71 |
| XIVa | 4-Cl-C₆H₄- | S | 116 |

PREPARATION OF THE INTERMEDIATES

Example Ib

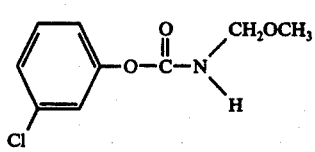

A few drops of triethylamine were added to 128.6 g (1 mole) of 3-chlorophenol in 150 ml of carbon tetrachloride. 95.8 g (1.1 moles) of methoxymethyl isocyanate were then added dropwise in such a way that the temperature could be kept at between 40° and 60° C. The mixture was stirred for a further 15 hours at room temperature and was concentrated by distilling off the solvent in vacuo. The red-brown oil which remained was taken up in chloroform and was washed repeatedly with sodium carbonate solution and then with water until neutral. The organic phase was dried over sodium sulphate and concentrated in vacuo by distilling off the solvent. 167 g (77.5% of theory) of N-methoxymethyl-carbamic acid 3-chlorophenyl ester were obtained as a yellow oil.

The compounds listed in Table 3 which follows were prepared analogously:

Table 3

$$R^1-X-\overset{\overset{O}{\|}}{C}-\underset{H}{N}-CH_2OCH_3 \quad (V)$$

| Example No. | R¹ | X | Melting point (° C) |
|---|---|---|---|
| IIb | 2-Cl-C₆H₄- | O | 54 |
| IIIb | 2,4-diCl-C₆H₃-CH₂- | O | 44 |
| IVb | 2,4-di-C(CH₃)₃-5-CH₃-C₆H₂- | O | 182 |
| Vb | biphenyl-4-yl | O | 89 |
| VIb | naphthalen-1-yl | O | 82 |
| VIIb | 3,4-diCl-C₆H₃- | O | 99 |
| VIIIb | 2,6-diCl-C₆H₃- | O | 92 |
| IXb | 2-(isopropoxy)-C₆H₄- | O | 52 |
| Xb | 2,6-di(CH₃)-4-(CH₃S)-C₆H₂- | O | 70 |
| XIb | 4-Cl-C₆H₄-CH₂- | O | 62 |
| XIIb | 2,4-diCl-5-NO₂-C₆H₂- | O | 124 |
| XIIIb | 4-CH₃O-C₆H₄- | O | 73 |
| XIVb | 4-Cl-C₆H₄- | S | 90 |

Table 3-continued $$R^1-X-\overset{O}{\underset{\|}{C}}-N\diagup\overset{CH_2OCH_3}{\diagdown H}\quad (V)$$

| Example No. | $R^1$ | X | Melting point (° C) |
|---|---|---|---|
| XVb | phenyl-C(CH_3)(CH_3)-phenyl- | O | $n_{20}^D$ 1.5564 |
| XVI | 2,4-dichlorobenzyl (Cl-phenyl(Cl)-CH_2-) | O | 55 |
| XVIIb | phenyl- | O | $n_{20}^D$ 1.5154 |
| XVIIIb | 3-methylphenyl- | O | $n_{20}^D$ 1.5123 |

It will be understood that the specification and examples are illustrative but not limitative of the present invention and that other embodiments within the spirit and scope of the invention will suggest themselves to those skilled in the art.

What is claimed is:

1. Phenoxycarboxylic acid aryloxy carbonylaminomethyl ester compound of the formula $$R^1-X-\overset{O}{\underset{\|}{C}}-N\diagup\overset{CH_2-O-\overset{O}{\underset{\|}{C}}-\underset{R^2}{\overset{|}{CH}}-(CH_2)_n-O-R^3}{\diagdown H}\quad (I)$$

wherein

R$^1$ is phenyl, substituted phenyl, where the substituent is a halogen, alkyl group of 1 to 4 carbon atoms, alkoxy group with 1 to 4 carbon atoms, alkyl(thio) with 1 to 4 carbon atoms, phenyl, phenoxy or trifluoromethyl group, benzyl, substituted benzyl, where the substituent is a halogen atom substituted on the phenyl ring thereof, an alkyl group of 1 to 4 carbon atoms substituted on the phenyl ring thereof, an alkoxy group with 1 to 4 carbon atoms substituted on the phenyl ring thereof, an alkyl(thio) group with 1 to 4 carbon atoms substituted on the phenyl group thereof, a phenyl, phenoxy or trifluoromethyl group substituted on the phenyl ring thereof, naphthyl or substituted naphthyl where the substituent is 1 or more halogen, alkyl with 1 to 4 carbon atoms, alkoxy with 1 to 4 carbon atoms, alkyl(thio) with 1 to 4 carbon atoms, phenyl, phenoxy or trifluoromethyl group, R$^2$ is hydrogen or alkyl of from 1 to 4 carbon atoms, R$^3$ is phenyl or substituted phenyl, where the substituent is 1 or more halogen, straight or branch chain alkyl with 1 to 4 carbon atoms, alkoxy with 1 or 2 carbon atoms, halogenoalkyl with 1 to 2 carbon atoms, and 1 to 5 halogen atoms nitro or phenoxy which itself can be substituted by fluorine, chlorine, bromine or nitro, X is oxygen, and n is 0, 1 or 2.

2. Phenoxycarboxylic acid aryloxycarbonylaminomethyl ester compound as claimed in claim 1 wherein R$^1$ is phenyl.

3. Phenoxycarboxylic acid aryloxycarbonylaminomethyl ester compound as claimed in claim 1 wherein R$^1$ is substituted phenyl wherein the substituents are selected from halogen, alkyl of from 1 to 4 carbon atoms, alkoxy of from 1 to 4 carbon atoms, alkylthio of from 1 to 4 carbon atoms, phenyl, phenoxy and trifluoromethyl.

4. Phenoxycarboxylic acid aryloxycarbonylaminomethyl ester compound as claimed in claim 1 wherein R$^1$ is benzyl or substituted benzyl wherein the substitutents are selected from halogen, alkyl of from 1 to 4 carbon atoms, alkoxy of from 1 to 4 carbon atoms, alkylthio of from 1 to 4 carbon atoms, phenyl, phenoxy and trifluoromethyl.

5. Phenoxycarboxylic acid aryloxycarbonylaminomethyl ester compound as claimed in claim 1 wherein R$^1$ is napthyl or substituted napthyl wherein the substituents are selected from halogen, alkyl of from 1 to 4 carbon atoms, alkoxy of from 1 to 4 carbon atoms, alkylthio of from 1 to 4 carbon atoms, phenyl, phenoxy and trifluoromethyl.

6. Phenoxycarboxylic acid aryloxycarbonylaminomethyl ester compound as claimed in claim 1 wherein R$^2$ is hydrogen.

7. Phenoxycarboxylic acid aryloxycarbonylaminomethyl ester compound as claimed in claim 1 wherein R$^2$ is alkyl of from 1 to 2 carbon atoms.

8. Phenoxycarboxylic acid aryloxycarbonylaminomethyl ester compound as claimed in claim 1 wherein R$^3$ is phenyl.

9. Phenoxycarboxylic acid aryloxycarbonylaminomethyl ester compound as claimed in claim 1 wherein R$^3$ is substituted phenyl wherein the substituents are selected from halogen, alkyl of from 1 to 4 carbon atoms, alkoxy of from 1 to 2 carbon atoms, haloalkyl of from 1 to 2 carbon atoms, and 1 to 5 halo atoms, nitro, phenoxy, halophenoxy and nitrophenoxy.

10. Compound as claimed in claim 1 of the formula

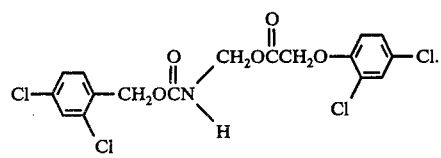

11. Compound as claimed in claim 1 of the formula

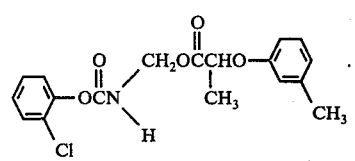

12. Compound as claimed in claim 1 of the formula

13. Compound as claimed in claim 1 of the formula

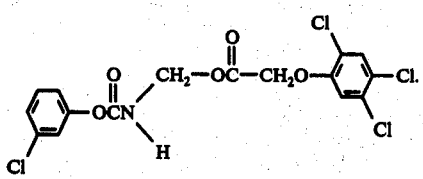

14. Compound as claimed in claim 1 of the formula

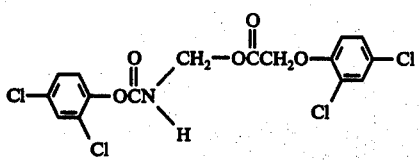

15. Compound as claimed in claim 1 of the formula

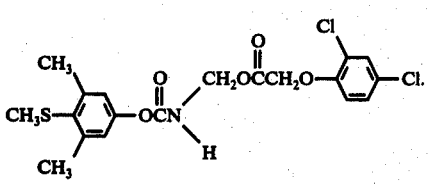

16. Plant growth regulant composition comprising a plant growth regulantly acceptable carrier and, 0.1 to 95 percent by weight of a compound of the formula

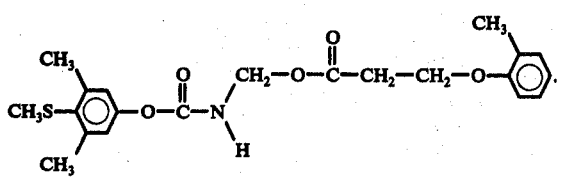

wherein
R$^1$ is phenyl, substituted phenyl, where the substituent is a halogen, alkyl group of 1 to 4 carbon atoms, alkoxy group with 1 to 4 carbon atoms, alkyl(thio) with 1 to 4 carbon atoms, phenyl, phenoxy or trifluoromethyl group, benzyl, substituted benzyl, where the substituent is a halogen atom substituted on the phenyl ring thereof, an alkyl group of 1 to 4 carbon atoms substituted on the phenyl ring thereof, an alkoxy group with 1 to 4 carbon atoms substituted on the phenyl ring thereof, an alkyl(thio) group with 1 to 4 carbon atoms substituted on the phenyl group thereof, a phenyl, phenoxy or trifluoromethyl group substituted on the phenyl ring thereof, naphthyl or substituted naphthyl where the substituent is 1 or more halogen, alkyl with 1 to 4 carbon atoms, alkoxy with 1 to 4 carbon atoms, alkyl(thio) with 1 to 4 carbon atoms, phenyl, phenoxy or trifluoromethyl group,
R$^2$ is hydrogen or alkyl of from 1 to 4 carbon atoms,
R$^3$ is phenyl or substituted phenyl, where the substituent is 1 or more halogen, straight or branch chain alkyl with 1 to 4 carbon atoms, alkoxy with 1 or 2 carbon atoms, halogenoalkyl with 1 to 2 carbon atoms, and 1 to 5 halogen atoms nitro or phenoxy which itself can be substituted by fluorine, chlorine, bromine or nitro,
X is oxygen, and
$n$ is 0, 1 or 2.

17. Method of regulating the growth of plants which comprises applying to the plants or their habitat 0.01 to 50 kg per hectare of a compound of the formula

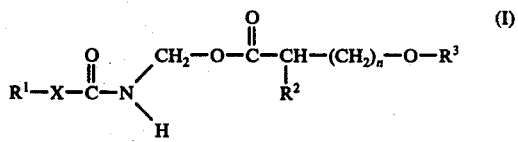

wherein
R$^1$ is phenyl, substituted phenyl, where the substituent is a halogen, alkyl group of 1 to 4 carbon atoms, alkoxy group with 1 to 4 carbon atoms, alkyl(thio) with 1 to 4 carbon atoms, phenyl, phenoxy or trifluoromethyl group, benzyl, substituted benzyl, where the substituent is a halogen atom substituted on the phenyl ring thereof, an alkyl group of 1 to 4 carbon atoms substituted on the phenyl ring thereof, an alkoxy group with 1 to 4 carbon atoms substituted on the phenyl ring thereof, an alkyl(thio) group with 1 to 4 carbon atoms substituted on the phenyl group thereof, a phenyl, phenoxy or trifluoromethyl group substituted on the phenyl ring thereof, naphthyl or substituted naphthyl where the substituent is 1 or more halogen, alkyl with 1 to 4 carbon atoms, alkoxy with 1 to 4 carbon atoms, alkyl(thio) with 1 to 4 carbon atoms, phenyl, phenoxy or trifluoromethyl group,
R$^2$ is hydrogen or alkyl of from 1 to 4 carbon atoms,
R$^3$ is phenyl or substituted phenyl, where the substituent is 1 or more halogen, straight or branch chain alkyl with 1 to 4 carbon atoms, alkoxy with 1 or 2 carbon atoms, halogenoalkyl with 1 to 2 carbon atoms, and 1 to 5 halogen atoms nitro or phenoxy which itself can be substituted by fluorine, chlorine, bromine or nitro,
X is oxygen, and
$n$ is 0, 1 or 2.

18. Method of regulating plant growth as claimed in claim 17 wherein R$^2$ in the formula is hydrogen; or alkyl of from 1 to 2 carbon atoms.

19. Method of regulating plant growth as claimed in claim 17 wherein said compound is selected from those of the following formulas:

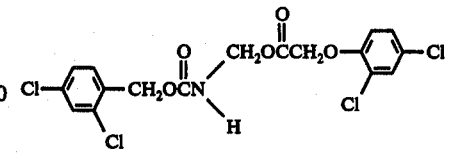

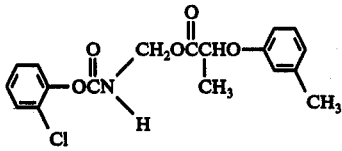

-continued
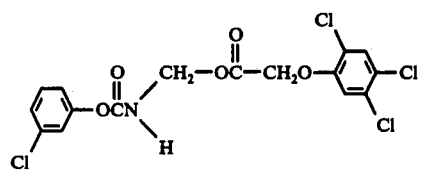
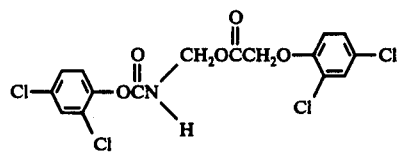
-continued
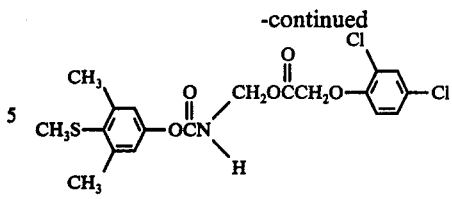
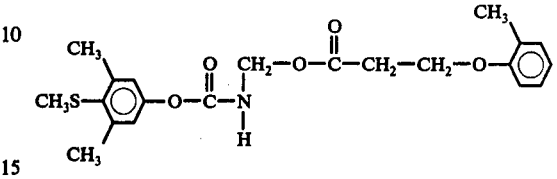
20. Method as claimed in claim 17 wherein said compound is applied to inhibit plant growth.
21. Method as claimed in claim 17 wherein said compound is applied to promote plant growth.
22. Method as claimed in claim 17 wherein said compound is applied to alter plant growth.
* * * * *

UNITED STATES PATENT AND TRADEMARK OFFICE
CERTIFICATE OF CORRECTION

PATENT NO. : 4,090,862
DATED : May 23, 1978
INVENTOR(S) : Rudolf Thomas et al

It is certified that error appears in the above-identified patent and that said Letters Patent are hereby corrected as shown below:

Column 9, line 2, "kalolins" should read -- kaolins --.

Column 14, line 63, "0105" should read -- 0.05 --.

Column 26, line 55, "135" should read -- 133 --.

Signed and Sealed this

Fourteenth Day of November 1978

[SEAL]

Attest:

RUTH C. MASON
Attesting Officer

DONALD W. BANNER
Commissioner of Patents and Trademarks